United States Patent [19]

Koch

[11] Patent Number: 4,752,301

[45] Date of Patent: Jun. 21, 1988

[54] METHOD TO DUE COTTON AND OTHER SUBSTRATES WITH A MICRO-ORGANISM BIOMASS CONTAINING INDIGO

[75] Inventor: Werner Koch, Oberwil, Switzerland

[73] Assignee: Sandoz Ltd., Basel, Switzerland

[21] Appl. No.: 65,801

[22] Filed: Jun. 23, 1987

[30] Foreign Application Priority Data

Jun. 23, 1986 [DE] Fed. Rep. of Germany ....... 3620915

[51] Int. Cl.$^4$ .......................... C09B 7/00; C09B 61/00; C12P 17/10
[52] U.S. Cl. ........................................... 8/653; 8/646; 8/918; 435/121; 435/118
[58] Field of Search ..................... 8/653, 646; 435/121

[56] References Cited

U.S. PATENT DOCUMENTS 4,520,103  5/1985  Ensley ................................. 435/121

*Primary Examiner*—A. Lionel Clingman
*Attorney, Agent, or Firm*—Gerald D. Sharkin; Richard E. Vila; Thomas C. Doyle

[57] ABSTRACT

A biomass containing biologically produced indigo or a derivative thereof which is used for dyeing without isolating the indigo dye from the rest of the solid biomass before dyeing. Cotton dyeings of clean pure shade can be obtained by a vat dyeing procedure which have the usual fastness properties associated with the active substance.

9 Claims, No Drawings

METHOD TO DUE COTTON AND OTHER SUBSTRATES WITH A MICRO-ORGANISM BIOMASS CONTAINING INDIGO

The invention relates to a biomass containing indigo or a derivative thereof produced by bacterial cells. Such a biomass allows the so-produced indigo compound to be used commercially in a dyebath without the need for the indigo to be isolated in pure form.

According to the invention, there is provided a method for dyeing a substrate comprising applying to the substrate a biomass containing indigo (or a derivative thereof) in which the dye has been produced by a microorganism without isolating the dye from the rest of the solid biomass before dyeing.

It is known to produce and isolate indigo from indole or tryptophan via indole by microbiological sources. Such biosyntheses for example are described in U.S. Pat. No. 4,520,103; Science Vol. 222, 1983, pages 167 to 169; and BIOTECHNOLOGY Vol. 4, 1986, pages 321 to 324. The contents of each of these references are incorporated herewith by reference.

In all the references isolation of the water-insoluble indigo which is produced in or outside the cells is described as being carried out by repeated extraction with boiling chloroform. From a commercial point of view however, this is too time consuming and expensive, and the same would be true of alternative isolation methods which might be used. This would make dyeing with microbiologically prepared indigo isolated from the rest of the biomass commercially unfeasible.

One of the advantages of the present invention is that one can commercially apply the indigo dye, produced by a microbiological source to a substrate without the need to isolate the dye from the rest of the biomass, or to purify the dye further or to concentrate the dye prior to dyeing.

Preferably a method for dyeing a substrate according to the invention comprises producing indigo (or a derivative thereof) by a microorganism to form a biomass;

lysing the cells of the biomass; and dyeing the substrate with the solid biomass without isolating the indigo (or its derivative) from the rest of the solid biomass.

Lysing the membrane can be carried out by known mechanical or preferably non-mechanical methods such as (a) acid-base reaction (as described in Example 1)
(b) reaction under mild pressure
(c) osmolysis or
(d) enzymatic reaction.

Preferably in a method according to the invention, irrespective of the chosen lysing process, the biomass can be further treated to ensure that all the cells of the biomass have been denatured (this is desirable for ecological reasons) with aqueous sodium hydroxide solution to bring the pH alkaline (preferably around 12), followed by neutralization for example by treating with a hydrogen phosphate to bring the pH to 7.

Preferably in a method according to the invention, after biosynthesis but prior to dyeing, the solid biomass is dried. Drying of the biomass may be effected in any conventional manner, for example it can be dried on a sheet metal, in a vacuum furnace or with a vacuum paddle drier equipped with a stirring cylinder to distill off the water. Preferably, drying is effected by spraying.

For this spray drying the biomass is first passed through a sieve of particular particle size and then dried to a powder using a conventional spray dryer, for example a Buchi sprayer, or is dried in a fluidised bed to form a granular material. This drying step may be carried out in the presence of further auxiliaries, such as solubilising or standardising agents that are useful in the following dyeing process.

Preferably prior to drying the excess liquid phase, which does not contain indigo, is separated from the solid biomass by known techniques, such as centrifugation, decantation and/or coarse filtration.

Preferably, in a method according to the invention, after biosynthesis and any separation but prior to drying, the biomass is homogenised by known methods, preferably at pH 7, for example by intense stirring (with a polythron stirrer), with a diluent or by a milling process (e.g. with glass beads) optionally in the presence of a dispersing agent, preferably an anionic dispersing agent, more preferably a dispersing agent suitable for increasing the dispersibility of indigo (or a derivative thereof) in the particular dyebath in which the dye is to be used. This has the effect of reducing the size of any solid agglomerations of indigo formed outside the cells.

Further, according to the invention, there is provided a process for preparing a biomass containing indigo (or a derivative thereof) suitable for addition to a dyebath comprising producing indigo (or a derivative thereof) by a microorganism; and drying the resulting biomass, whereby the indigo dye is not isolated from the rest of the biomass prior to addition to the dyebath.

Preferably in a process for preparing the biomass according to the invention, prior to drying, lysing of the cells of the biomass is carried out. Further prior to drying separation and/or homogenisation of the biomass as described above may be carried out.

Further, according to the invention there is provided a substantially dry biomass containing indigo (or a derivative thereof) produced by a microorganism whereby the inidgo dye has not been separated from the rest of the biomas. Such a biomass is suitable for addition to a dyebath without any isolation, purification or concentrating operations.

One advantage of drying the biomass prior to use in a dyebath is that the pungent smell is virtually eliminated.

Preferably the microbiologically produced indigo compound used according to this invention is a compound of formula I, $$\text{I}$$

in which each $R_1$, independently, is hydrogen or $C_{1-4}$alkyl (e.g. methyl);

each $R_2$, independently is hydrogen, fluorine, chlorine bromine, $C_{1-4}$alkyl (e.g. methyl), $C_{1-4}$alkoxy (e.g. methoxy), hydroxy, cyano, amino or nitro.

By this formula symmetrically as well as asymmetrically substituted indigo analogues are included.

According to the biosyntheses described above, indigo is formed from indole by cloned recombinant *Esch-*

*erichia coli* cells. If, instead of indole, a substituted indole or indole mixture is used, the symmetrically or asymmetrically substituted indigo derivatives may be obtained which can be used to dye cotton.

The indigo compounds in form of a biomass obtained according to this invention are suitable for dyeing hydroxy group- or nitrogen-containing organic substrates, such as wool, cotton or linen in a vat dyeing process, preferably using the immersion process according to an indigo dyeing plant with ventilation. The crude vat dye is reduced to its water-soluble form and is applied to the substrate where it is fixed by oxidation. A dyeing is obtained having the usual fastness properties associated with the active substance.

Dyeing with a biomass according to the invention produces pure indigo (or derivatives thereof) dye nuances with the usual fastness properties associated with the active substance.

It is surprisingly found that dyeing with the crude indigo containing debris of the biomass nevertheless gives a clean pure coloured dyeing. Effectively it appears as if purification of the dye occurs on the substrate, rendering purification at an earlier stage unnecessary.

The following Examples illustrate the invention. In the Examples all parts and all percentages are by weight or volume, and the temperatures given are in degrees Centigrade, unless indicated otherwise.

EXAMPLE 1

Production of Indigo-Biomass

Cells of *Escherichia coli* strain HB 101 transformed with Plasmid PE317 as described in U.S. Pat. No. 4,520,103 are cultured in a fermenter under the conditions described in Example 5 of said patent.

The wet fermenter paste obtained by pouring off the fermentation liquid is centrifuged to remove further liquid. Subsequently, the cells are lysed by an acid-base reaction. The pH is made alkaline by adding aqueous sodium hydroxide solution, and then brought to pH 7 by adding disodium hydrogen phosphate.

After cell lysis, the biomass is treated with aqueous sodium hydroxide solution at pH 12, and finally the pH is adjusted to 7 by adding disodium phosphate. An aqueous suspension with an unpleasant smell is obtained containing indigo active ingredient, cell fragments, sodium phosphate, and by-products resulting from the fermentation process as well as remaining nutrient solution.

Further microbiologically produced indigo dyes (starting from appropriately substituted indole derivatives) may be prepared according to the method described in Example 1 upon addition of the desired indole derivative starting material to the culture medium.

EXAMPLE 2

Drying of the Indigo Suspension to Powder

Prparations for spray drying can be made up by one of the following methods (a) to (d) below:

(a) The aqueous suspension obtained in Eample 1 which has been homogenised by a polythron stirrer, is passed as such through a sieve having a mesh size of 0.1 mm. The suspension passes easily through, and an insignificant residue is left.

(b) The aqueous suspension which contains agglomeration of particles is treated in a dissolver (an apparatus equipped with a high-speed toothed disk), whereby the particles distributed in the suspension are reduced to small pieces.

(c) The aqueous suspension of Example 1 is subjected to bead milling (without the addition of any further additives).

(d) The aqueous suspension of Example 1 is subjected to bead milling in the presence of an anionic dispersing agent. A suitable dispersing agent is the sodium salt of the condensation product obtained by reacting aqueous $\beta$-naphthalene sulphonic acid with formaldehyde.

EXAMPLE 3

(a) Drying can be carried out as follows on a Büchi sprayer: The indigo suspension, resulting from one of the pre-treatments of Example 2a to 2d above, is sprayed along with a hot air stream of 130° through a double nozzle. The temperature of the hot air is then reduced, and the spent air is about 75°. A dark powder is obtained which is free of ingredients of disagreeable smell.

(b) Drying of the indigo suspension to form granules can be carried out as follows:

The pre-treatment is effected by one of the methods of Example 2. The indigo suspension thus pre-treated is sprayed in a fluidised bed granulator in conventional manner. Dark granules are obtained which are free of ingredients of disagreeable smell.

EXAMPLE 4

Indigo dyeing according to the immersion process (simulated indigo dyeing plant) may be carried out as follows:

(a) Production of the dye liquor: The dye is dissolved in accordance with the principles of a stock vat process. By this method, 100 parts by weight of the powder or granules obtained in Example 3a or 3b, and 20 parts by volume of sodium sulphoricinoleate (80% sulphonation degree), a commercially available anionic liquid dispersing agent, are pasted together thoroughly. To this paste, soft water at 60° is added, and the volume is adjusted to 100 parts. Then 0.75 part by volume of a sodium hydroxide solution (36° Bé) and 0.6 part by weight of concentrated aqueous sodium hydrosulphite solution are added. The mixture is held for 15 minutes at 60°. A light yellow vat is obtained which is cooled to 25° and employed as such (i.e., the whole batch) in the following dyeing process.

(b) Dyeing can be carried out as follows: A boiled and easily wettable cotton fabric is immersed into the dye liquor prepared according to Example 4a for 10 seconds. The cotton fabric is then squeezed out through two rollers on a foulard resulting in a toal pick-up of ca. 60% (by increase of dry weight). The vat dye absorbed by the fabric is oxidised by suspending in air for three minutes to yield a blue dye.

With respect to an indigo dyeing plant the above operations represent one strike. It is necessary to repeat these operations twice so that for the completed dyeing a total of three strikes are performed.

The resulting dyeing is then rinsed with cold water until it is alakli-free. By treating with 1.5 ml/l of 40% hydrogen peroxide over five minutes at 60° the oxidation is completed and the dyeing is rinsed with warm water. Soaping is then carried out for five minutes at 80° using 1 ml/l of an aliphatic polyglycol ether, a commercially available non-ionic dispersing agent. The dyeing is rinsed first with warm and then with cold water and dried in conventional manner.

A strong indigo blue dyeing is obtained showing a clear and pure shade. The fastness properties of this cotton dyeing fully correspond to those expected for a dyeing made with conventionally prepared indigo.

What is claimed is:

1. A method for dyeing a substrate comprising applying to the substrate a biomass containing indigo or a derivative thereof in which the dye has been produced by a microorganism without isolating the dye from the rest of the solid biomass before dyeing.

2. A method according to claim 1 comprising
   producing indigo or a derivative thereof by a microorganism to form a biomass;
   lysing the cells of the biomass; and
   dyeing the substrate with the solid biomass without isolating the indigo or its derivative from the rest of the solid biomass.

3. A method according to claim 2 comprising drying a solid biomass containing indigo or a derivative thereof prior to dyeing.

4. A method according to claim 3 in which the biomass is dried by a sprayer to form a powder or in a fluidised bed to form granules.

5. A method according to claim 3 in which the biomass is homogenised after producing indigo or a derivative thereof but prior to drying.

6. A method according to claim 1 in which the substrate is a hyroxy group- or nitrogen-containing organic substrate.

7. A method according to claim 6 in which the substrate is cotton.

8. A method according to claim 1 whereby the dyeing method is a vat dyeing method.

9. A substrate dyed by a method according to claim 1.

UNITED STATES PATENT AND TRADEMARK OFFICE
CERTIFICATE OF CORRECTION

PATENT NO. : 4,752,301
DATED      : June 21, 1988
INVENTOR(S): Werner Koch

It is certified that error appears in the above-identified patent and that said Letters Patent is hereby corrected as shown below:

Add the following claim:

-- 10. A method according to claim 2 wherein the biomass contains indigo or a derivative thereof in which the indigo compound is a compound of formula I,

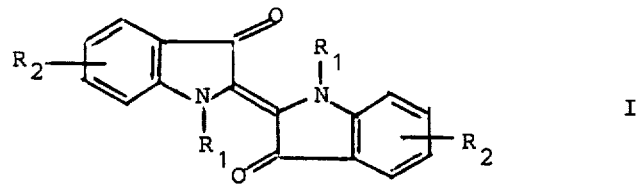

I in which each $R_1$, independently, is hydrogen or $C_{1-4}$ alkyl;
and each $R_2$, independently, is hydrogen, fluorine, chlorine, bromine, $C_{1-4}$ alkyl, $C_{1-4}$ alkoxy, hydroxy, cyano, amino or nitro. --

Signed and Sealed this

Sixth Day of March, 1990

Attest:

JEFFREY M. SAMUELS

Attesting Officer

Acting Commissioner of Patents and Trademarks